United States Patent [19]

Tanaka et al.

[11] Patent Number: 4,663,520

[45] Date of Patent: May 5, 1987

[54] FAIL-SAFE LASER APPARATUS INCLUDING MAIN AND SAFETY SHUTTERS FOR LASER

[75] Inventors: Shinya Tanaka; Masaru Sato, both of Tokyo, Japan

[73] Assignee: Tokyo Kogaku Kikai Kabushiki Kaisha, Tokyo, Japan

[21] Appl. No.: 725,674

[22] Filed: Apr. 22, 1985

[30] Foreign Application Priority Data

May 2, 1984 [JP] Japan ................................. 59-87772

[51] Int. Cl.$^4$ ............................................... G01J 1/32
[52] U.S. Cl. .................................... 250/205; 250/498.1
[58] Field of Search .................. 219/121 LA, 121 LB; 250/205, 498.1; 372/14, 29, 37

[56] References Cited

U.S. PATENT DOCUMENTS 4,415,231 11/1983 Kaczensky et al. ......... 250/498.1 X
4,543,477 9/1985 Doi et al. ....................... 250/205 X Primary Examiner—Eugene R. LaRoche
Assistant Examiner—James C. Lee
Attorney, Agent, or Firm—Pahl, Lorusso & Loud

[57] ABSTRACT

A fail-safe laser apparatus includes a laser beam radiation source for emitting a laser beam along an optical axis, a main shutter for intercepting or attenuating the laser beam incident thereon in its closed position, and a safety shutter for completely intercepting the laser beam incident thereon in its closed position. The main shutter is moved to its open position in coagulating the diseased part. A first sensor produces a first signal indicative of the intensity of the laser beam emitted along the optical axis between the radiation source and the main shutter. A second sensor produces a second signal indicative of the intensity of the laser beam emitted along the optical axis between the main shutter and the safety shutter. A detection circuit is responsive to the first and second signals for actuating a safety shutter control means to move the safety shutter to its open position in accordance with the first and second signals.

17 Claims, 2 Drawing Figures

FAIL-SAFE LASER APPARATUS INCLUDING MAIN AND SAFETY SHUTTERS FOR LASER

BACKGROUND OF THE INVENTION

This invention relates to a laser apparatus including a main optical shutter adapted to attenuate or intercept a laser beam emitted from a laser beam radiation source and, more particularly, to a fail-safe laser apparatus including a safety optical shutter in addition to the main optical shutter to completely intercept the laser beam incident thereon in the event of failure of the main optical shutter.

Continuous radiation type laser beam radiation sources have been employed in machine tools, medical machines such as laser scalpels and laser coagulators, and length measuring machines. It is normal practice to provide a mechanical shutter movable between open and closed positions for interrupting the laser beam from a laser beam radiation source. In the event of failure of the mechanical shutter, however, the laser beam is emitted at an unexpected time, putting a person in danger. This is serious particularly for medical machines.

OBJECT OF THE INVENTION

Therefore, the object of the present invention is to provide a fail-safe laser apparatus which can completely intercept laser beam radiation in the event of failure of a main mechanical shutter.

SUMMARY OF THE INVENTION

There is provided, in accordance with the present invention, a fail-safe laser apparatus which includes a laser beam radiation source for emitting a laser beam along an optical axis. The laser apparatus comprises a main shutter movable between its open and closed positions for attenuating or intercepting the laser beam incident thereon in its closed position. The main shutter is moved to its open position in coagulating the diseased part. A safety shutter is additionally provided for completely intercepting the laser beam incident thereon in its closed position. A first sensor is sensitive to the laser beam emitted along the optical axis between the radiation source and the main shutter for producing a first signal indicative of a sensed laser beam intensity. A second sonsor is sensitive to the laser beam emitted along the optical axis between the main shutter and the safety shutter for producing a second signal indicative of a sensed laser beam intensity. A detection circuit is responsive to the first and second signals for actuating a safety shutter control means to move the safety shutter to its open position in accordance with the first and second signals.

BRIEF DESCRIPTION OF THE DRAWINGS

This invention will be described in greater detail by reference to the following description taken in connection with the accompanying drawings, in which.

DETAILED DESCRIPTION OF THE PREFERRED EMBODIMENTS

Figure 1:
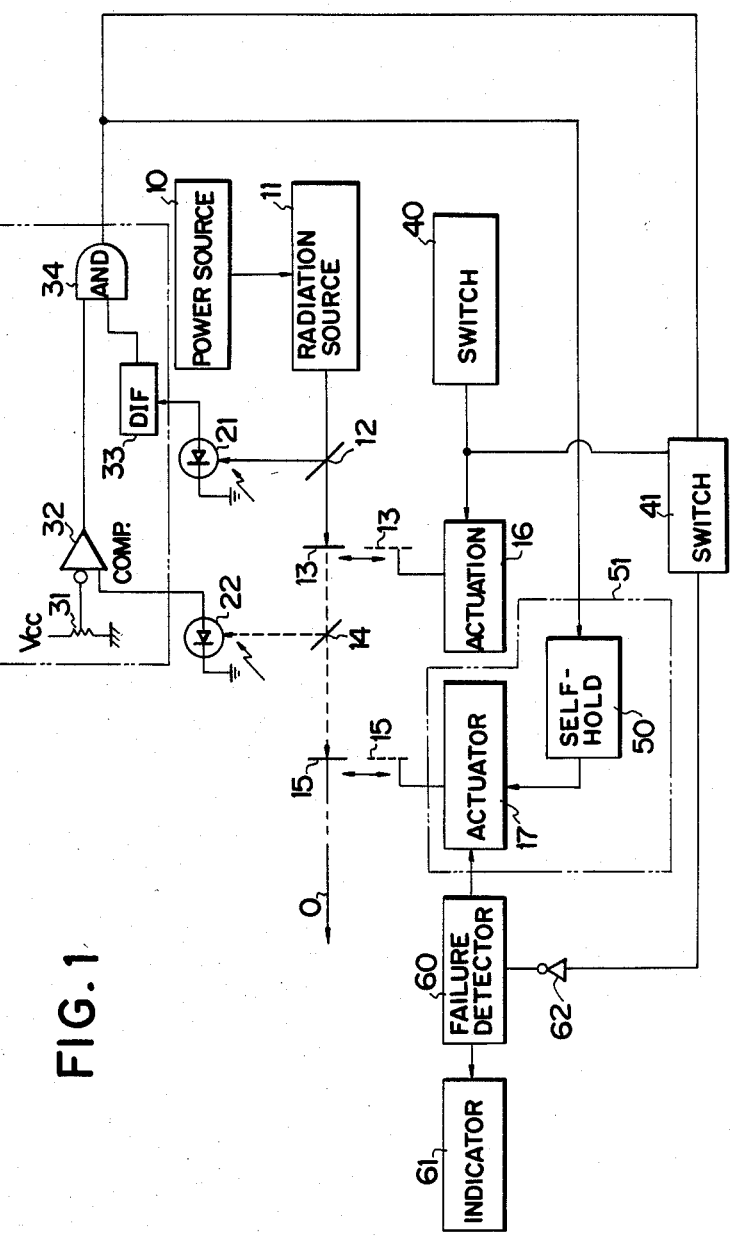
FIG. 1 is a schematic block diagram showing a fail-safe laser apparatus made in accordance with a first embodiment of the present invention.

With reference to the drawings, where like numerals refer to like parts in the views, and in particular to FIG. 1, there is shown a schematic block diagram of a laser apparatus embodying the present invention. The laser apparatus includes a laser beam radiation source 11 which is actuated by a power source 10 to emit a laser beam or wave along an optical axis O. A main optical shutter 13 is normally located along the optical axis O, so as to function as an optical filter for transmitting only several percents of beam energy therethrough. The main optical shutter 13 is effective to attenuate the laser beam energy to a minimum possible level required during adjustment in directing the optical axis to the diseased part (not shown). The main optical shutter 13 is moved, by a main shutter actuator 16, out of the optical axis O to the dotted line position shown when an operator manually turns an emission switch 40 on to generate a high or logic 1 signal to the main shutter actuator 16 for the purpose of coagulating the diseased part. The switch 40 may be associated with a timer (not shown) which is triggered by the logic 1 signal from the emmisionswitch 40 and is timed out to turn the switch 40 off a predetermined time after the switch 40 is turned on.

A safety optical shutter 15 is provided in advance of the main optical shutter 13. The safety optical shutter 15 is made of metal and is normally located in the optical path O to prevent completely transmission of the laser beam therethrough. The safety optical shutter 15 is moved out of the optical path O to the dotted line position shown by a control means 51 to be described later in detail.

The laser apparatus also includes first and second half mirrors 12 and 14 which are positioned at the opposite sides of the main optical shutter 13 in the optical axis O. The first and second half mirrors 12 and 14 have a small reflectance at the wavelength of the laser beam radiation source 11. Consequently, a large parcentage of the beam energy is transmitted through the first and second half mirrors 12 and 14. The first half mirror 12 is tilted with respect to the optical axis O so as to reflect a small percentage of the beam energy toward a first photodiode 21. The first photodiode 21 generates a voltage signal to a detection circuit 30 upon reception of the beam energy reflected on the first half mirror 12. Similarly, the second half mirror 14 is tilted with respect to the optical axis O so as to reflect a small percentage of the beam energy toward a second photodiode 22. The second photodiode 22 generates a voltage signal to the detection circuit 30 upon reception of the beam energy reflected on the second half mirror 14.

The detection circuit 30 includes a differentiation circuit 33 which is coupled to the output terminal of the first photodiode 21 for differentiating the voltage signal fed thereto from the first photodiode 21. The differentiation circuit 33 generates a high or logic 1 output signal to one input terminal of an AND gate 34 when the first phtodiode 21 receives the laser beam reflected on the first half mirror 12. The AND gate 34 has another input terminal connected to the output terminininal of a comparator circuit 32 which has an input terminal connected to the second photodiode 22 and another input terminal connected to a potentiometer 31. The potentiometer 31 is connected between a voltage source Vcc and electrical ground for supplying a reference voltage to the comparator 32. The reference voltage may be, by sliding a potentiomemter wiper arm, to a level which corresponds to a level of the voltage signal generated at the output terminal of the second photodiode 22 when the laser beam is attenuated properly through the main optical shutter 13. The comparator circuit 32 generates a high or logic 1 output signal to the AND gate 34 when the voltage signal fed from the second photodiode 22 is less than the reference voltage. The AND gate 34 generates a logic 1 signal at its output terminal only when it receives logic 1 signals at both of its input terminals. In other words, the AND gate 34 generates a logic 1 output signal only when the two conditions are fulfilled, that is, when the laser beam radiation source 11 emits a laser beam, and the emitted laser beam is attenuated properly by the main optical shutter 13. The output terminal of the AND gate 34 is connected to the safety shutter control circuit or means 51.

The safety shutter control circuit or means 51 includes a self-hold circuit 50 which responds to a logic 1 signal fed from the AND gate 34 to generate a drive signal to the safety shutter actuator 17 which thereby moves the safety optical shutter 15 out of the optical axis O to the dotted line position. Thereafter, the self-hold circuit 50 retains the drive signal regardless of the output of the AND gate 34. The self-hold circuit 50 may be arranged to release the held condition when the power source 10 is turned off.

Preferably, the output terminal of the AND gate 34 is connected through a switch 41 and an inverter 62 to a failure detection circuit 60. (An EOR gate may be used in place of the switch 41.) The switch 41 has an input terminal connected to the switch 40. The switch 41 is turned off when the switch 40 is turned on. The inverter 62 inverts the signal from the AND circuit 34 to generate a logic 1 signal. Upon application of a logic 1 signal to the failure detection circuit 60, it causes the actuator 17 to place the safety optical shutter 15 in its closed position and also actuates an indicator 61 to provide a failure indication on an indicator 61. The failure detection circuit 60 is effective to provide a failure indication on the indicator 61 upon occurrence of a failure such as radiation source abnormal oscillation, main shutter operation failure, radiation source power failure, or the like before the switch 40 is turned on. It is to be noted that the failure detection circuit 60 and its related elements may be omitted for simplification of the laser apparatus.

The operation is as follows. It is first assumed that the main and safety optical shutters 13 and 15 are in the closed positions as indicated by solid lines prior to application of power to the laser beam radiation source 11 from the power source 10. When the power source 10 is turned on, the laser beam radiation source 11 emits a laser beam toward the first half mirror 12 which reflects a small percentage of the laser beam energy to the first photodiode 21. As a result, the first photodiode 21 produces a voltage signal which is differentiated in the differentiation circuit 33 to produce a logic 1 signal which is applied to the AND gate 34. A large percentage of the laser beam energy emitted from the radiation source 11 is transmitted through the first half mirror 12 to the main optical shutter 13 which attenuates the received laser beam energy to a proper level. The second half mirror 14 receives the attenuated laser beam energy and reflects a small percentage of the received laser beam energy to the second photodiode 22. Consequently, the second photodiode 21 produces a voltage signal which is compared in the comparator circuit 32 with a reference voltage applied from the potentiometer 31. If the main optical shutter 13 is in order and it attenuates the received laser beam energy to a proper level, the voltage signal is less than the reference voltage and thus the comparator circuit 32 generates a logic 1 signal, causing the AND gate 34 to generate a logic 1 signal.

The logic 1 signal is applied from the AND gate 34 to the self-hold circuit 50 which thereby drives the actuator 17, causing movement of the safety optical shutter 15 out of the optical path O to the dotted line position, so that the attenuated laser beam can be directed toward the diseased part.

If the main optical shutter 13 is in its open position for any of reasons, the second half mirror 14 will receive unattenuated laser beam and thus the second photodiode 22 generates a voltage signal greater than the reference voltage. Consequently, the comparator circuit 32 generates a logic O signal to block the AND gate 34. As a result, the self-hold circuit 50 receives a logic O signal from the AND gate and it retains the actuator 17 out of operation. The logic O signal is also applied from the AND gate 34 to the EOR gate 41 which generates a logic O signal since the switch 40 is off. The logic O signal is converted in the inverter 62 to a logic 1 signal which is applied to the failure detection circuit 60. As a result, the failure detection circuit 60 prevents the actuator 17 from moving the safety optical shutter 15 out of the optical path O and provides a failure indication on the indicator 61.

If the main optical shutter 13 is subject to failure causing deterioration of its ability to attenuate the received laser beam energy or the laser beam radiation source 11 is subject to failure causing radiation of excessive laser beam energy, the second photodiode 22 will generate a voltage signal greater than the reference voltage. Consequently, the failure detection circuit 60 prevents the actuator 17 from moving the safety optical shutter 15 and provides a failure indication on the indicator 61 in the same manner as described above.

If a power failure occurs, the laser beam radiation source 11 will exit no laser beam energy. Consequently, the first photodiode 21 generates no voltage signal and thus the differentiation circuit 33 generates a logic O signal to the AND gate 34. As a result, the self-hold circuit 50 receives a logic O signal from the AND gate 34 and maintains the actuator 17 out of operation. The logic O signal is applied from the AND gate 34 to the switch 41 which generates a logic O signal since the switch 40 is off. The logic O signal is converted in the inverter 62 to a logic 1 signal which is applied to the failure detection circuit 60. As a result, the failure detection circuit 60 prevents the actuator 17 from moving the safety optical shutter 15 out of the optical path O and provides a failure indication on the indicator 61.

When an operator turns the switch 40 on for the purpose of coagulating the diseased part after the attenuated laser beam is directed to the diseased part, a logic 1 signal is applied to the main shutter actuator 16 which thereby moves the main optical shutter 13 out of the optical path O to the dotted line position, permitting radiation of unattenuated laser beam toward the diseased part. This movement of the main optical shutter 13 causes an increase in the voltage signal applied from the second photodiode 22 over the reference voltage applied from the potentiometer 31. As a result, the output of the comparator circuit 32 changes to a logic O level and thus the output of the AND gate 34 changes to a logic O level. Although the logic 1 signal is applied to the self-hold circuit 50, it retains the previously established condition and holds the safety optical shutter 15 is the open position. The logic 1 signal is also applied from the AND gate 34 to the switch 41. However, as the switch 40 is on, the switch 41 is off so that the signal is not sent to the inverter 62. Consequently, the failure detection circuit 60 has no effect on the operation of the safety shutter actuator 17 and provides no failure indication on the indicator 61.

The switch 40 is turned off by a timer or like device (not shown), causing the main shutter actuator 16 to move the main optical shutter 13 to its closed position a predetermined time after the switch 40 is once turned on. Since the self-hold circuit 50 retains the safety optical shutter 15 in its open position, the subsequent cycles of the coagulation operation can be started merely by turning the switch 40 on to open the main optical shutter 13.

Figure 2:
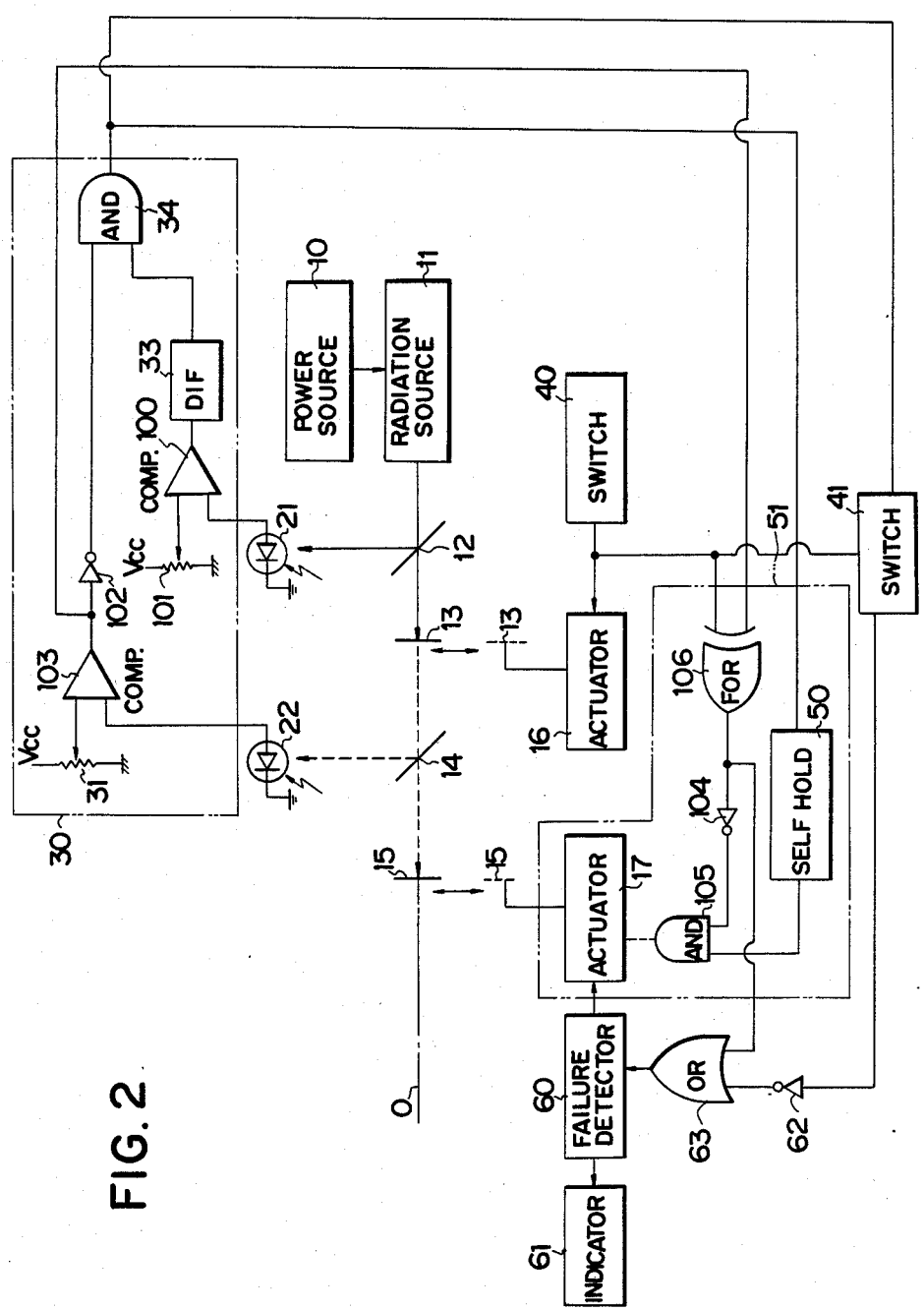
FIG. 2 is a schematic block diagram showing a second embodiment of the present invention.

Referring now to FIG. 2, an alternative embodiment of the present invention is illustrated with the same elements being designated by the same reference numerals.

In this embodiment, the detection circuit 30 includes a comparator circuit 100 which has an input terminal connected to the output terminal of the first photodiode 21 and another input terminal connected to a potentiometer 101. The potentiometer 101 is connected between a voltage source Vcc and electrical ground for supplying a reference voltage to the comparator circuit 100. The reference voltage may be changed, by sliding the potentiometer's wiper arm, to a level which corresponds to a level of the voltage signal generated at the output terminal of the first photodiode 21 when the laser beam radiation source 11 operates in order. The comparator circuit 100 generates a logic 1 signal at its output terminal only when the voltage signal applied from the first photodiode 21 exceeds the reference voltage. The output terminal of the comparator circuit 100 is coupled to the differentiation circuit 33 which, in turn, is connected to one input terminal of the AND circuit 34.

In FIG. 2, the reference numeral 103 designates a comparator circuit which has an input terminal coupled to the output terminal of the second photodiode 22 and another input terminal connected to the potentiometer 31 which supplies a reference voltage corresponding to a level of the voltage signal generated at the output terminal of the second photodiode 22 when the laser beam is attenuated properly through the main optical shutter 13, as described hereinbefore. The comparator circuit 103 generates a logic 1 signal at its output terminal only when the voltage signal applied from the second photodiode 22 exceeds the reference voltage. The output terminal of the comparator circuit 103 is coupled through an inverter 102 to another input terminal of the AND gate 34 and also directly to an Exclusive Or (EOR) gate 106 which has another input terminal connected to the switch 40. The output terminal of the EOR gate 106 is connected through an inserter 104 to one input terminal of an AND gate 105. The AND gate 34 generates a logic 1 signal at its output terminal only when it receives logic 1 signals at the respective input terminals thereof. In other words, the AND gate 34 generages a logic 1 output signal only when the two conditions are fulfilled, that is, when the laser beam radiation source 11 emits a laser beam at a level greater than a predetermined level, and the emitted laser beam is attenuated by the main optical shutter 13 to a level less than a predetermined level.

The output terminal of the AND gate 34 is coupled to one input terminal of the switch 41 which has another input terminal connected to the switch 40. The output terminal of the switch 41 is coupled through the inverter 62 to one input terminal of an OR gate 63 which is connected at another input terminal to the output terminal of the EOR gate 106. The output terminal of the OR gate 63 is connected to the failure detection circuit 60. The output terminal of the AND gate 34 is also connected to the self-hold circuit 50 which, in turn, is connected to another input terminal of the AND gate 105. The output terminal of the AND gate 105 is connected to the safety shutter actuator 17. An EOR gate may be used in place of the switch 41. It is to be noted that the failure detection circuit including the failure detector 60 may be removed for simplification of the laser apparatus.

The operation is as follows: it is first assumed that the main and safety optical shutters 13 and 15 are in the closed positions as indicated by solid lines prior to application of power to the laser beam radiation source 11 from the power source 10. When the power source 10 is turned on, the laser beam radiation source 11 starts emitting a laser beam toward the first half mirror 12 which reflects a small percentage of the laser beam energy to the first photodiode 21. As a result, the first photodiode 21 produces a voltage signal which is compared in the comparator circuit 100 with a reference voltage applied from the potentiometer 101. If the laser beam radiation source 11 operates in order, that is, the emitted laser beam energy is equal to or greater than a level required for diseased part coagulation, the comparator circuit 100 generates a logic 1 signal. The differentiation circuit 33 differentiates this logic 1 signal and generates a logic 1 signal to the AND gate 34.

A large percentage of the laser beam energy emitted from the radiation source 11 is transmitted through the first half mirror 12 to the main optical shutter 13 which attenuates the received laser beam energy to a proper level. The second half mirror 14 receives the attenuated laser beam energy and reflects a small percentage of the received laser beam energy to the second photodiode 22. Consequently, the second photodiode 22 generates a voltage signal which is compared in the comparator circuit 103 with a reference voltage applied from the potentiometer 31. If the main optical shutter 13 is in its closed position and attenuates the received laser beam energy to the proper level, the voltage signal is equal to or less than the reference voltage and thus the comparator circuit 103 generates a logic O signal. This logic O signal is converted by the inverter 102 to a logic 1 signal which is applied to cause the AND gate 34 to generate a logic 1 signal.

This logic 1 signal is applied from the AND gate 34 to the self-hold circuit 50 which thereby generates a logic 1 signal and retains this condition thereafter. The logic O signal is applied from the comparator circuit 103 to one input terminal of the EOR gate 106. The EOR gate 106 generates a logic O signal since it receives, at another input terminal thereof, a logic O signal from the switch 40 which still remains off. This logic O signal is applied to the inverter 104 which converts it to a logic 1 signal, causing the AND gate 105 to generate a logic 1 signal to the safety shutter actuator 17. As a result, the actuator 17 moves the safety optical shutter 15 out of the optical path O to the dotted line position.

Under this condition, the OR gate 63 receives logic O signals at both of its input terminals and provides a logic O signal to the failure detection circuit 60. Consequently, the failure detection circuit 60 has no effect on the operation of the safety shutter actuator 17 and provides no failure indication on the indicator 61.

If the main optical shutter 13 is in its open position for any of reasons, the second half mirror 14 will receive unattenuated laser beam and thus the second photodiode 22 generates a voltage signal geater than the reference voltage given by the potentiometer 31. Consequently, the comparator circuit 103 generates a logic 1 signal which is converted by the inverter circuit 102 to a logic O signal to block the AND gate 34. As a result, the AND gate 34 generates a logic O signal to the self-hold circuit 50 which thereby blocks the AND gate 105 to retain the safety shutter actuator 17 out of operation and also through the switch 41 to the inverter circuit 62 which converts it to a logic 1 signal. This logic 1 signal causes the failure detection circuit 60 to prevent the safety shutter actuator 17 from moving the safety optical shutter 15 out of the optical path O to the dotted line position and also to provide a failure indication on the indicator 61. As a result, the safety optical shutter 15 provides a complete interception to the unattenuated laser beam.

If the main optical shutter 13 is subject to failure causing deterioration of its ability to attenuate the received laser beam energy or the laser beam radiation source 11 is subject to failure causing radiation of excessive laser beam energy, the second photodiode 22 will generate a voltage signal greater than the reference voltage given from the potentiometer 31. Consequently, the self-hold circuit 50 blocks the AND gate 105 to prevent the safety shutter actuator 17 from moving the safety optical shutter 15 to its open position and the failure detection circuit 60 provides a failure indication on the indicator 61 in the same manner as described above.

It is therefore apparent that the safety device of the invention can provide a complete interception to the laser beam when a failure occurs in the laser apparatus upon actuation of the laser beam radiation source.

If the main optical shutter 13 moves to its open position in the event of failure of the main shutter actuator 16 during the attenuated laser beam radiation, the output of the comparator circuit 103 will change to the logic 1 level, causing a change of the output of the EOR gate 106 to a logic 1 level since it receives a logic O signal is converted by the inverter 104 to a logic O signal which blocks the AND gate 105 to cause the safety shutter actuator 17 thereby to move the safety optical shutter 17 to its closed position so as to completely intercept the laser beam toward the patient. The logic 1 signal is also applied from the EOR gate 106 through the OR gate 63, causing the failure detection circuit 60 to provide a failure indication on the indicator 61.

When the operator turns the switch 40 on for the purpose of coagulating the dieased part after the attenuated laser beam is directed to the diseased part, a logic 1 signal is applied to the main shutter actuator 16 which thereby moves the main optical shutter 13 out of the optical path O to the dotted line position, permitting radiation of unattenuated laser beam toward the diseased part. This movement of the main optical shutter 13 causes an increase in the voltage signal applied from the second photodiode 22 over the reference voltage applied from the potentiometer 31. As a result, the output of the comparator circuit 103 changes to a logic 1 level. The logic 1 signal is applied from the comaprator circuit 103 to the inverter circuit 102 which converts it to a logic O signal to block the AND gate 34. The logic 1 signal is also applied form the comparator circuit 103 to the EOR gate. The EOR gate 106 generates a logic O signal since it receives a logic 1 signal from the switch 40 which is turned on. This logic O signal is converted by the inverter circuit 104 to a logic 1 signal which is applied to the AND gate 105.

Under this condition, the AND gate 34 generates a logic O signal to the self-hold circuit 50. Since the self-hold circuit 50 retains its output at the logic 1 level, the AND gate 105 generates a logic 1 signal, causing the safety shutter actuator 17 to move the safety optical shutter 15 out of the optical path O to the dotted line position. The logic O signal is also applied form the AND gate 34 to the switch 41. However the switch 41 is off since the switch 40 is on. Consequently, the failure detection circuit 60 has no effect on the operation of the safety shutter actuator 17 and provides no failure indication on the indicator 61.

If the main optical shutter 13 does not move to its open position in spite of the fact that the operator turns the switch 40 on, the output of the comparator circuit 103 will remain at the logic O level which is applied to one input terminal of the EOR gate 106. The EOR gate 106 receives, at another input terminal thereof, a logic 1 signal from the switch 40 which is now turned on and it generates a logic 1 signal at its output terminal. The logic 1 signal is converted by the inverter 104 to a logic O signal which blocks the AND gate 105 to cause the safety shutter actuator 17 to move the safety optical shutter 17 to its closed position so as to completely intercept the laser beam toward the patient.

It is to be noted that the main optical shutter 13 may be replaced by a shutter made of metal or the like which can completely intercept a laser beam if another laser optical device is used in directing the optical axis O to the diseased part. In this case, the potentiometer 31 is set to provide a zero voltage reference to the comparator circuit 13 or 103.

It is therefore apparent from the foregoing that there has been provided, in accordance with the present invention, a fail-safe laser apparatus for completely intercepting laser beam radiation from a laser beam radiation source in the event of failure of the main optical shutter that fully satisfies the objects, aims and advantages set forth above. The fail-safe laser apparatus operates in a photoelectric fashion in order to optimize the time response to the occurence of failure of the main optical shutter as compared to a mechanically operated apparatus. In addition, the fail-safe laser apparatus operates in response to laser beam energy rather than main optical shutter position in order to detect main optical shutter characteristic deterioration.

While the present invention has been described in connection with a medical laser apparatus, it is to be understood, of course, that the present invention may be applied to any other laser apparatus. In addition, while this invention has been described in connection with specific embodiments thereof, it is evident that many alternatives, modifications and variations will be apparent to those skilled in the art. Accordingly, it is intended to embrace all alternatives, modifications and variations that fall within the broad scope of the appended claims.

What is claimed is:

1. A fail-safe laser apparatus for emitting a laser beam along an optical axis, comprising:
   a laser beam radiation source;
   a main shutter movable between open and closed positions for attenuating in its closed position a laser beam emitted from said laser beam radiation source along said optical axis;
   a safety shutter movable between open and closed positions for completely intercepting the laser beam incident thereon in its closed position, said safety shutter remaining in said open position in normal operation of the laser apparatus in which all components are properly functioning;
   said main shutter being positioned between said laser beam radiation source and said safety shutter along said optical axis;
   a first sensor for monitoring at least a part of said laser beam emitted from said laser beam radiation source between said laser beam radiation source and said main shutter to produce a first signal indicative of a sensed laser beam intensity;
   a second sensor for monitoring at least a part of said laser beam between said main shutter and said safety shutter to produce a second signal indicative of a sensed laser beam intensity;
   a detection circuit for receiving said first and second signals to detect whether said laser beam radiation source emits said laser beam along said optical axis and whether said main shutter attenuates said laser beam emitted from said laser beam radiation source, thereby to produce a third signal indicative of detected results; and
   a safety shutter control means for receiving said third signal from said detection circuit to control movement of said safety shutter between its open and closed positions.

2. A fail-safe laser apparatus as defined in claim 1, further comprising:
   first actuating means for moving said main shutter between its open and closed positions;
   an emission switch connected to said first actuating means in such a way that said first actuating means may move said main shutter to its open position only when said emission switch is on; and
   second actuating means included in said safety shutter control means for moving said safety shutter to its closed position when no power is supplied to said laser beam radiation source.

3. A fail-safe laser apparatus as claimed in claim 1, wherein said detection circuit includes means for detecting said first signal from said first sensor and said second signal from said second sensor to produce said third signal as a control signal for moving said safety shutter to its open position only when said second signal is equal to or less than a predetermined reference value.

4. A faile-safety laser apparatus as claimed in claim 3, wherein said predetermined reference value corresponds to an intensity of the laser beam attenuated by said main shutter in its closed position.

5. A fail-safe laser apparatus as claimed in claim 1, wherein said safety shutter control means includes:
   self-hold means responsive to said third signal from said detection circuit for producing a drive signal and thereafter retaining said drive signal; and
   actuating means responsive to said drive signal for moving said safety shutter to its open position.

6. A fail-safe laser apparatus as claimed in claim 3, wherein said safety shutter control means includes:
   self-hold means responsive to said control signal for producing a drive signal and thereafter retaining said drive signal; and
   actuating means responsive to said drive signal for moving said safety shutter to its open position.

7. A fail-safe laser apparatus as claimed in claim 1, wherein said detection circuit includes means for comparing said second signal with a predetermined reference value, means for receiving a signal from said comparing means to produce a control signal only when said second signal is greater than said reference value whereby said safety shutter control means is actuated to move said safety shutter to its closed position on the basis of said control signal.

8. A fail-safe laser apparatus as claimed in claim 7, wherein said predetermined reference value corresponds substantially to an intensity of the laser beam attenuated by said main shutter in its closed position.

9. A fail-safe laser apparatus as defined in claim 1, further comprising:
   first actuating means for moving said main shutter between its open and closed positions;
   an emission switch connected to said first actuating means in such a way that said first actuating means may move said main shutter to its open position only when said emission switch is on; and
   second actuating means included in said safety shutter control means for moving said safety shutter to its closed position when said third signal received by said safety shutter indicates an abnormal condition of said apparatus.

10. A fail-safe laser apparatus for emitting a laser beam along an optical axis, comprising:
    a laser beam radiation source;
    a main shutter movable between open and closed positions for completely intercepting in its closed position a laser beam emitted from said laser beam radiation source along said optical axis;
    a safety shutter movable between open and closed positions for completely intercepting the laser beam incident thereon in its closed position, said safety shutter remaining in said open position in normal operation of the laser apparatus in which all components are properly functioning;
    said main shutter being positioned between said laser beam radiation source and said safety shutter along said optical axis;
    a first sensor for monitoring at least a part of said laser beam emitted from said laser beam radiation source between said laser beam radiation source and said main shutter to produce a first signal indicative of a sensed laser beam intensity;
    a second sensor for monitoring at least a part of said laser beam between said main shutter and said safety shutter to produce a second signal indicative of a sensed laser beam intensity;
    a detection circuit for receiving said first and second signals to detect whether said laser beam radiation source emits said laser beam along said optical axis and whether said main shutter intercepts said laser beam emitted from said laser beam radiation source, thereby to produce a third signal indicative of detected results; and
    a safety shutter control means for receiving said third signal from said detection circuit to control movement of said safety shutter between its open and closed positions.

11. A fail-safe laser apparatus as defined in claim 10, further comprising:
   first actuating means for moving said main shutter between its open and closed positions;
   an emission switch connected to said first actuating means in such a way that said first actuating means may move said main shutter to its open position only when said emission switch is on; and
   second actuating means included in said safety shutter control means for moving said safety shutter to its closed position when no power is supplied to said laser beam radiation source.

12. A fail-safe laser apparatus as claimed in claim 10, wherein said detection circuit includes means for detecting said first signal from said first sensor and said second signal from said second sensor to produce said third signal as a control signal for moving said safety shutter to its open position only when said second signal is zero.

13. A fail-safe laser apparatus as claimed in claim 10, wherein said safety shutter control means includes:
   self-holding means responsive to said third signal from said detection circuit for producing a drive signal and thereafter retaining said drive signal; and
   actuating means responsive to said drive signal for moving said safety shutter to its open position.

14. A fail-safe laser apparatus as claimed in claim 12, wherein said safety shutter control means includes:
   self-holding means responsive to said control signal for producing a drive signal and thereafter retaining said drive signal; and
   actuating means responsive to said drive signal for moving said safety shutter to its open position.

15. A fail-safe laser apparatus as claimed in claim 10, wherein said detection circuit includes means for comparing said second signal with a predetermined reference value, means for receiving a signal from said comparing means to produce a control signal only when said second signal is greater than said reference value whereby said safety shutter control means is actuated to move said safety shutter to its closed position on the basis of said control signal.

16. A fail-safe laser apparatus as claimed in claim 15, wherein said predetermined reference value is zero.

17. A fail-safe laser apparatus as defined in claim 10, further comprising:
   first actuating means for moving said main shutter between its open ad closed positions;
   an emission switch connected to said first actuating means in such a way that said first actuating means may move said main shutter to its open position only when said emission switch is on; and
   second actuating means included in said safety shutter control means for moving said safety shutter to its closed position when said third signal received by safety shutter indicates an abnormal condition of said apparatus.

* * * * *

UNITED STATES PATENT AND TRADEMARK OFFICE
CERTIFICATE OF CORRECTION

PATENT NO. : 4,663,520
DATED : May 5, 1987
INVENTOR(S) : Shinya Tanaka and Masaru Sato It is certified that error appears in the above—identified patent and that said Letters Patent is hereby corrected as shown below:

Col. 1, line 50, "sonsor" should read -- sensor --.

Col. 2, line 40, "parcentage" should read -- percentage --; and
line 60, "phtodiode" should read -- photodiode --.

Col. 5, line 3, "is" should read -- in --; (first occurrence)
line 60, "inserter" should read -- inverter --; and
line 65, "generages" should read -- generates --.

Col. 7, line 10, "geater" should read -- greater --; and
line 50, after "signal" insert: -- from the switch 40 which still remains off. The logic 1 signal --.

Col. 8, line 3, "comaprator" should read -- comparator --; and
line 18, "form" should read -- from --.

Col. 9, line 56 (claim 4, line 1) "faile-safety" should read -- fail-safe --.

Signed and Sealed this

Twentieth Day of October, 1987

*Attest:*

DONALD J. QUIGG

*Attesting Officer*     *Commissioner of Patents and Trademarks*